United States Patent [19]

Aoyagi et al.

[11] Patent Number: 4,832,484
[45] Date of Patent: May 23, 1989

[54] APPARATUS FOR DETERMINING THE CONCENTRATION OF A LIGHT-ABSORBING MATERIAL IN BLOOD

[75] Inventors: Takuo Aoyagi; Nobutaka Kobayashi; Tadashi Sasaki, all of Tokyo, Japan

[73] Assignee: Nihon Kohden Corporation, Tokyo, Japan

[21] Appl. No.: 113,969

[22] Filed: Oct. 29, 1987

[30] Foreign Application Priority Data

Oct. 29, 1986 [JP] Japan .................. 61-257668

[51] Int. Cl.⁴ .................................. G01N 33/48
[52] U.S. Cl. .............................. 356/41; 128/633
[58] Field of Search ............ 356/40, 41; 128/633, 128/634

[56] References Cited

U.S. PATENT DOCUMENTS 3,998,550 12/1976 Konishi et al. .............. 356/41
4,167,331 9/1979 Nielsen ........................ 356/40
4,714,341 12/1987 Hamaguri et al. ............ 356/41

OTHER PUBLICATIONS

I. Yoshiya, Y. Shimada, K. Tanaka, Spectrophotometric Monitoring of Arterial Oxygen Saturation, Med. & Bio. Eng. & Comp., pp. 27–32, 1–80.

Primary Examiner—Vincent P. McGraw
Attorney, Agent, or Firm—Sughrue, Mion, Zinn, Macpeak, and Seas

[57] ABSTRACT

An apparatus for determining the concentration of a light-absorbing material contained in blood flowing through a tissue which minimizes the amount of error caused by noise and which ensures highly precise results at all times. The apparatus operates according the principle that light beams of different wavelengths are absorbed by different amounts when passing through the tissue at different portions of the blood pulsation cycle. A plurality of points are detected that fall in the vicinity of the peak and trough of a cycle of a light detection signal. For each wavelength of light, the values of the detection signals produced at each of these points in time is stored. The concentration of the light-absorbing material is computed in response to the stored detection signals.

3 Claims, 4 Drawing Sheets

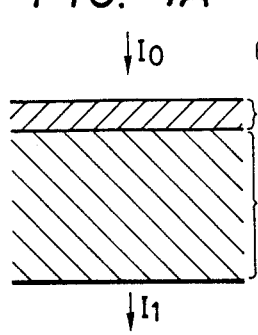
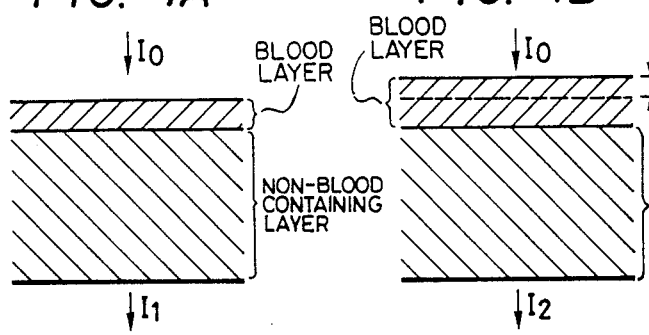
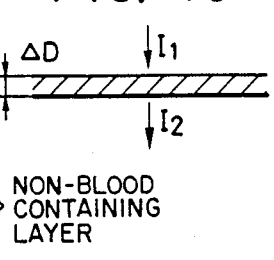
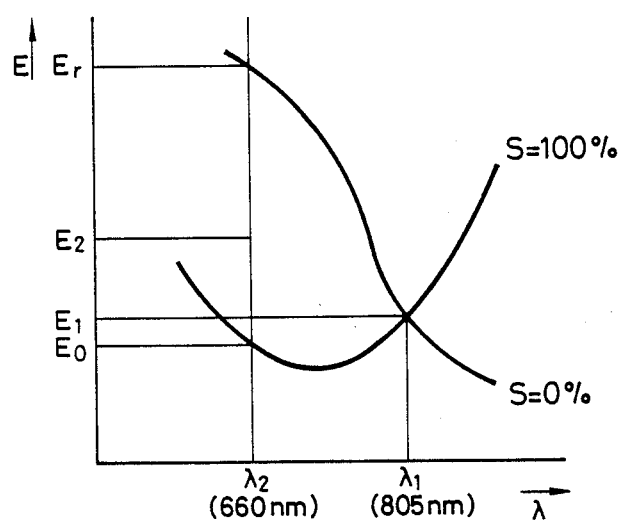

APPARATUS FOR DETERMINING THE CONCENTRATION OF A LIGHT-ABSORBING MATERIAL IN BLOOD

BACKGROUND OF THE INVENTION

The present invention relates to an apparatus for determining the concentration of a light-absorbing material in blood.

An oximeter is an example of an apparatus currently employed to determine the concentration of light-absorbing materials in blood. In a known type of oximeter, the oxygen saturation of blood in a living tissue sample is computer based on the fact that the relative quantities of two light beams having different wavelengths that pass through the tissue sample differ on account of blood pulsation. The operating principle of this type of oximeter is described hereinafter.

It is assumed first that a living tissue sample through which light is to pass is composed of a blood containing tissue layer and non-blood tissue layer as shown in FIG. 1A. In this case, the light attentuation by the overall tissue sample is expressed by:

$$-\log (I_1/I_0) = A + B \quad (1)$$

where
- $I_0$: the quantity of incident light,
- $I_1$: the quantity of transmitted light,
- A: the amount of light attenuation by the non-blood containing tissue, and
- B: the amount of light attenuation by the blood containing layer.

The light attenuation by the blood layer (B) is expressed by:

$$B = E \cdot C \cdot D \quad (2)$$

where
- E: the absorptivity coefficient of hemoglobin,
- C: the concentration of hemoglobin in blood, and
- D: the thickness of the blood layer.

Therefore, equation (1) can be rewritten as:

$$-\log (I_1/I_0) = A + E \cdot C \cdot D \quad (3)$$

The thickness of the blood layer D is variable due the normal arteiral blood pulsating. It is assumed that the thickness of the blood layer changes by $\Delta D$ as shown in FIG. 1B. If the quantity of light transmitted through the blood layer changed in thickness by $\Delta D$ is written as $I_2$, analogy with equation (3) gives:

$$-\log (I_2/I_0) = A + E \cdot C \cdot (D + \Delta D) \quad (4)$$

Subtracting equation (4) from equation (3), $$-\{\log (I_1/I_0) - \log (I_2/I_0)\} = -EC\Delta D,$$

or $$-\log (I_2/I_1) = EC\Delta D \quad (5)$$

As can be seen from equation (3), equation (5) is equivalent to the expression of light attenuation for the case where incident light having an intensity of $I_1$ passes through a blood containing layer with a thickness of $\Delta D$ to produce light transmission in a quantity $I_2$. This relation is depicted in FIG. 1C.

Next will be considered the case where two light beams having different wavelengthsare transmitted through a blood containing layer at the measurement site. FIG. 2 shows the relationship between the thickness of the blood containing layer D and each of $I_1$ (the quantity of transmitted light at a wavelength of $\lambda_1$) and $I_2$ (the quantity of transmitted light having a wavelength of $\lambda_2$). If the change in the thickness of the blood layer that occurs between two points in time $t_1$ and $t_2$ is written as $\Delta D$, and if the values of $I_1$ and $I_2$ at time $t_1$ are written as $I_{11}$ and $I_{12}$, respectively, with the values of I1 and I2 at time $t_2$ being written as $I_{21}$ and $I_{22}$, respectively, the following relations are established in consideration of equation (5):

For the first wavelength $\lambda_1$:

$$-\log (I_{21}/I_{11}) = E_1 C \Delta D \quad (6)$$

For the second wavelength $\lambda_2$:

$$-\log (I_{22}/I_{12}) = E_2 C \Delta D \quad (7)$$

where $E_1$ is the absorptivity coefficient of the blood for light at the wavelength $\lambda_1$ and $E_2$ is the absorptivity coefficient of the blood for light at the wavelength $\lambda_2$.

Equations (6) and (7) can be rewritten as follows:

$$\log (I_{11}/I_{21}) = E_1 C \Delta D \quad (8)$$

$$\log (I_{12}/I_{22}) = E_2 C \Delta D \quad (9)$$

Dividing equation (9) by equation (8) and writing the quotient as $\phi$, $$\phi = \{\log (I_{12}/I_{22})\}/\{\log (I_{11}/I_{21})\} = E_1/E_2 \quad (10)$$

Since equation (10) does not contain the term $\Delta D$, the times $t_1$ and $t_2$ may be any two values.

Equation (10) can be rewritten as;

$$E_2 = \phi \cdot E_1 \quad (11)$$

If the absorptivity coefficient $E_1$ in equation (11) is known, $E_2$ can be determined by calculating $\phi$. As equation (10) shows, $\phi$ can be determined by calculating log $(I_{11}/I_{21})$ and log $(I_{12}/I_{22})$, and as already mentioned, log $(I_{11}/I_{21})$ can be determined by measuring $I_{11}$ and $I_{21}$ (the quantities of transmitted light at the wavelength $\lambda_1$ at any two points in time), while log $(I_{12}/I_{22})$ can be determined by measuring $I_{12}$ and $I_{22}$ (the quantities of transmitted light at the wavelength $\lambda_2$ at the aforementioned any two points in time).

Since $$\log (I_{11}/I_{21}) = \log I_{11} - \log I_{21} \quad (12)$$

$$\log (I_{12}/I_{22}) = \log I_{12} - \log I_{22} \quad (13)$$

the logarithm of $I_{21}$ may be subtracted from the logarithm of $I_{11}$ to obtain log $(I_{11}/I_{21})$ while the logarithm of $I_{22}$ is subtracted from the logarithm of $I_{12}$ to obtain log $(I_{12}/I_{22})$.

Equation (12) can be rewritten as log $(I_{11}/I_{21}) = \log \{1 + (I_{11} - I_{21})/I_{21}\}$. Since $I_{11} \simeq I_{21}$, the following approximation is valid:

$$\log (I_{11}/I_{21}) = (I_{11} - I_{21})/I_{21} \quad (14)$$

In like manner, the following approximation is valid:

$$\log (I_{12}/I_{22}) = (I_{22} - I_{22})/I_{22} \quad (15)$$

Using $E_2$, the oxygen saturation S of blood may be calculated by the following procedures.

The absorptivity coefficient E of the blood versus the wavelength $\lambda$ of light with which a living body is irradiated is shown in FIG. 3 for S=0% and S=100%. The wavelength at which the curve for S=0% crosses the curve for S=100% is selected as the first wavelength $\lambda_1$, which falls at 805 nm in FIG. 3. The absorptivity coefficient $E_1$ for the light beam having the wavelength $\lambda_1$ is insensitive to changes in the oxygen saturation of blood S. Accordingly, a wavelength different from $\lambda_1$ is selected as the second wavelength $\lambda_2$, which falls, for instance, at 660 nm in FIG. 3. At the wavelength $\lambda_2$, the absorptivity coefficient assumes the value $E_r$ when S=0% and the value $E_0$ if S=100%. $E_2$ is a value between $E_0$ and $E_r$. Using $E_r$, $E_0$ and $E_2$, S can be calculated by the following equation:

$$S = (E_2 - E_r)/(E_0 - E_r) \quad (16)$$

An apparatus which determines the oxygen saturation S of blood using the procedure described above is shown schematically in FIG. 4. Detectors 1 and 2 receive light beams that have passed through a living tissue sample and which have wavelengths of $\lambda_1$ and $\lambda_2$, respectively, and produce output signals indicative of the intensities of the two beams. Variation computing circuits 3 and 4 compute the respective amounts of light attenuation on the basis of the changes in the detection signals produced by detectors 1 and 2 at two identical points in time. In other words, using $I_{11}$ and $I_{12}$ representing the quantities of transmitted light at time $t_1$, as well as $I_{21}$ and $I_{22}$ representing the quantities of transmitted light at time $t_2$ (see FIG. 2), the circuits 3 and 4 compute $\log (I_{11}/I_{21})$ and $\log (I_{12}/I_{22})$, respectively, which are the left side of equations (8) and (9). As a result, the variation in light attenuation due to the change in blood thickness ($\Delta D$) on the right side of each of equations (8) and (9) is determined. Using the calculation results produced by the circuits 3 and 4, a divider circuit 5 determines $\phi$ expressed by equation (10). In the next step, an oxygen saturation computing circuit 6 computes S from equations (11) and (12) using the value of $\phi$ calculated by the divider cirucit 5 and the preliminary stored values of $E_1$, $E_r$ and $E_0$ as indicated in FIG. 3.

The apparatus described above has the disadvantage that noise is unavoidably present in the signals produced by the detectors 1 and 2. Therefore, a single sampling will not yield a reliable value and the values obtained over several samplings must be averaged. However, the sampling for a single measurement can only be performed a finite number of times since the oxygen saturation of blood varies constantly. Furthermore, the two sets of data $I_{11}$ and $I_{12}$ and data $I_{21}$ and $I_{22}$ employed for the calculation by the variation computing circuits 3 and 4 are values obtained at any two respective arbitrary points in time $t_1$ and $t_2$, as shown in FIG. 2, and hence it sometimes occurs that the difference between $I_{11}$ and $I_{21}$ or between $I_{12}$ and $I_{22}$ is very small. If this happens, computation using the two sets of data $I_{11}$ and $I_{12}$ and data $I_{21}$ and $I_{22}$ will not produce highly precise results.

SUMMARY OF THE INVENTION

The present invention has been accomplished in order to solve these problems of the prior art. An object, therefore, of the present invention is to provide an apparatus for determining the concentration of a light-absorbing material in blood that minimizes the error caused by noise and which ensures highly precise results of computation under all conditions.

The stated object of the present invention can be attained by an apparatus for determining the concentration of a light-absorbing material in blood that comprises: a light detector for detecting the intensities of light beams having different wavelengths which have passed through a living tissue; time point detecting means for detecting, for each wavelength of light, a plurality of points in time that fall in the vicinity of one peak and one trough of the detection signal from said light intensity detector; memory means which stores, for each wavelength of light, the values of detection signals produced at each of said points in time as detected by said detecting means; and concentration computing means which computes the concentration of the light-absorbing material of interest in the blood sample on the basis of the values of the detection signals stored by the memory means.

In the apparatus of the present invention having the arrangement described above, the memory means stores, for each wavelength of light, a plurality of values that fall in the vicinity of the peak and trough of one cycle of a signal detected by the light intensity detector. The concentration computing means computes the concentration of the light-absorbing material of interest on the basis of the stored plurality of values. Accordingly, the apparatus of the present invention yields highly precise values of measurement.

BRIEF DESCRIPTION OF THE DRAWINGS

FIGS. 1A to 1C illustrate schematically a cross section of a tissue containing blood vessels;

FIG. 3 is a graph showing the relationship between absorptivity and wavelength;

DESCRIPTION OF THE PREFERRED EMBODIMENTS

A preferred embodiment of the present invention is hereunder described with reference to the accompanying drawings.

Figure 2:
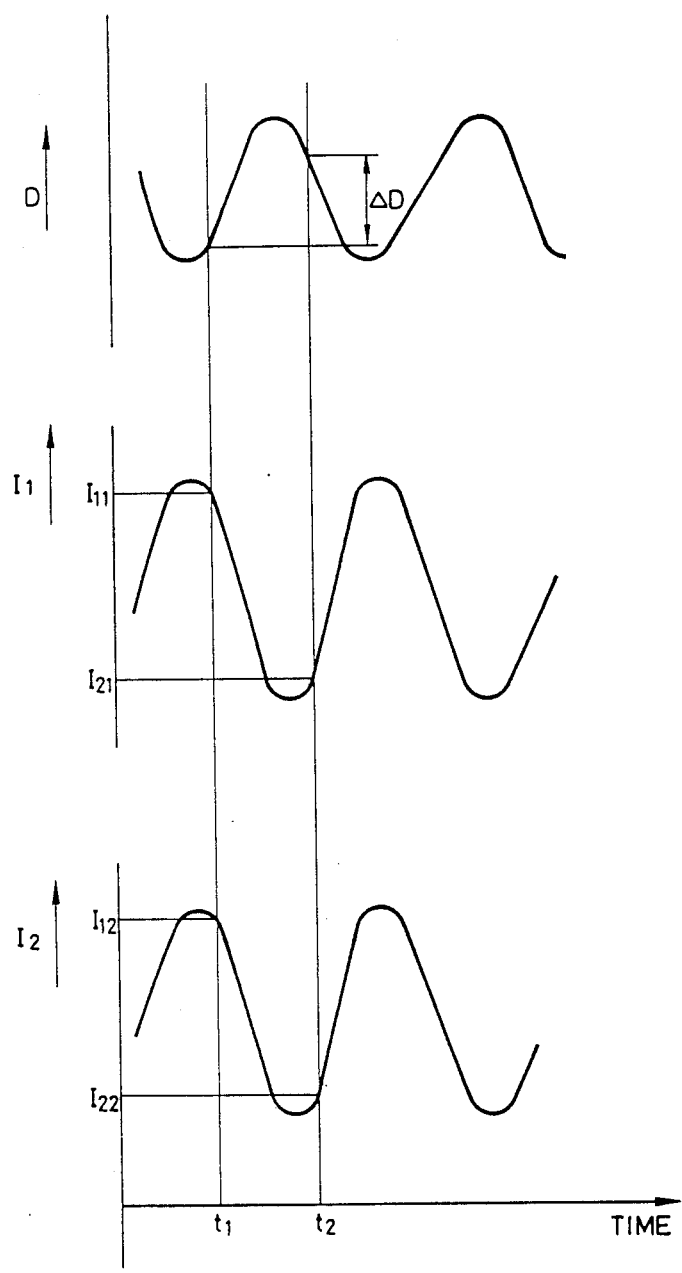
FIG. 2 is a waveform diagram showing changes in the thickness of the tissue of FIGS. 1A to 1C and intensities of two different light beams passing through the tissue.
Figure 4:
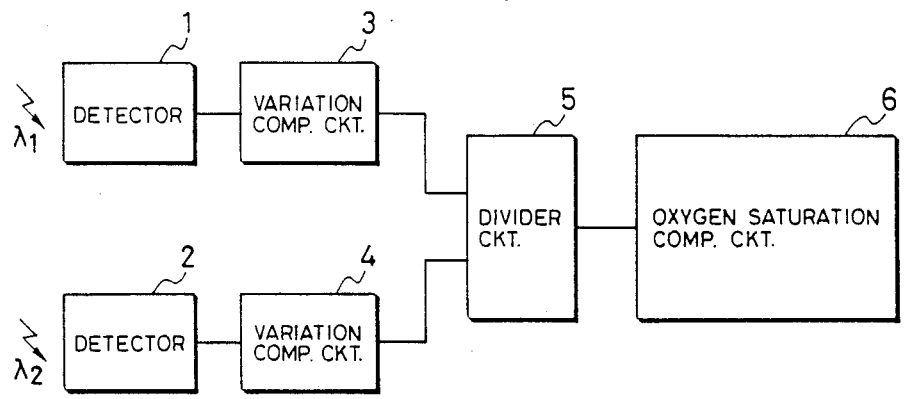
FIG. 4 is a schematic block diagram of a prior art oximeter.
Figure 5:
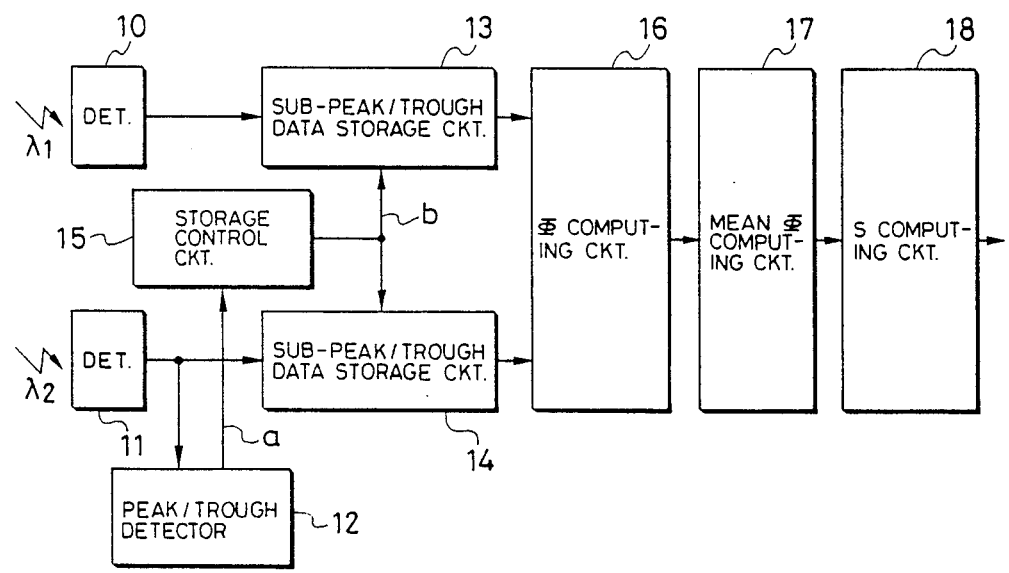
FIG. 5 is a schematic block diagram of an apparatus according to a preferred embodiment of the present invention.

FIG. 5 is a schematic block diagram of an oximeter constructed according to a preferred embodiment of the present invention. Shown at 10 and 11 in FIG. 5 are detectors that detect the intensities of light beams having wavelengths of $\lambda_1$ and $\lambda_2$ that have passed through part of a living tissue.

These detectors produce electrical signals that are indicative of the intensities of light $I_1$ and $I_2$ (see FIG. 6) having wavelengths $\lambda_1$ and $\lambda_2$, respectively. Shown at 12 is a peak/trough detector 12 which receives the output signal from the light intensity detector 11 and senses the peaks and troughs of that signal. Shown at 13 and 14 are sub-peak/trough data storage circuits, and 15 is a memory control circuit. In response to a signal a produced by the detector 12 when it senses the peaks and troughs of the signal output from the detector 11, the memory control circuit 15 produces a selected signal b at a predetermined timing relative to the signals a and supplies it to the sub-peak/trough data storage circuits 13 and 14. The sub-peak/trough data storage circuit 13 (14) stores the value of the signal produced by the light intensity detector 10 (11) a given time before or after the time when the circuit 13 (14) is supplied with the signal b from the memory control circuit 15.

Shown at 16 is a $\phi$ computing circuit which calculates $\phi$ in equation (10) using the data stored in the sub-peak/trough data storage circuits 13 and 14. Instead of calculating log $(I_{12}/I_{22})$/log $(I_{11}/I_{21})$ according to equation (10), the computing circuit 16 in the embodiment shown computes $(I_{11}-I_{21})/I_{21}$ and $(I_{12}-I_{22})/I_{22}$ using approximations (14) and (15) and determines the ratio of the computed values. Shown at 17 is a mean $\phi$ computing circuit which computes the mean average of the values of $\phi$ determined by the circuit 16. Shown at 18 is an S computing circuit which computes the oxygen saturation S on the basis of the mean $\phi$ calculated by the circuit 17. In the apparatus shown in FIG. 5, the peak/trough detector 12 and the memory control circuit 15 constitute a time-point detecting unit, and the $\phi$ computing circuit 16, mean $\phi$ computing circuit 17, and S computing circuit 18 together form a concentration computing unit.

The apparatus having the composition described above operates in the following manner.

Figure 6:
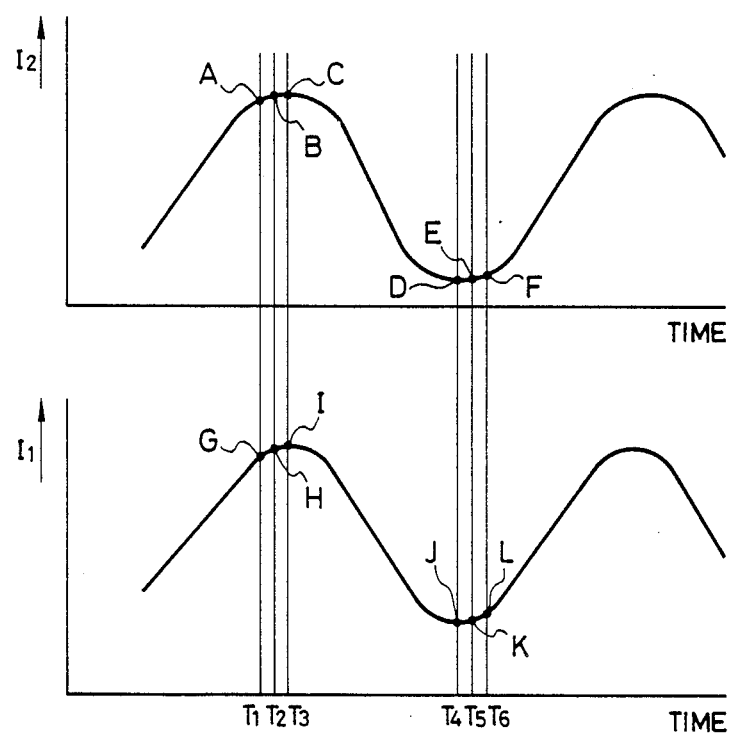
FIG. 6 shows graphically the detection signals from the two light intensity detectors shown in FIG. 5.

The light intensity detectors 10 and 11 detect the intensities $I_1$, and $I_2$ of received light beams having the wavelengths $\lambda_1$ and $\lambda_2$, respectively, and output detection signals having waveforms as shown in FIG. 6. The peak/trough detector 12 supplies the signal a to the memory control circuit 15 when it detects the peaks and troughs of the detection signal from the detector 11. Upon receiving the signal a, the memory control circuit 15 supplies the signal b to each of the sub-peak/trough data storage circuits 13 and 14 both at times $T_1$ to $T_3$ and at times $T_4$ to $T_6$ as counted from the reception of the signal a. Upon receiving the signal b, the sub-peak trough data storage circuits 13 and 14 store the values of the signals then produced by the detectors 10 and 11, respectively. Therefore, the circuit 13 stores values corresponding to the intensities of light of points G to L in FIG. 6, whereas the circuit 14 stores values corresponding to the intensities of light at points A to F in FIG. 6.

It should be noted that the peak/trough detector 12 used in the apparatus shown in FIG. 5 need not sense the absolute peaks and troughs of the signal from the detector 11; it suffices if the peak/trough detector 12 outputs the signal a when the detection signal from the detector 11 has reached an area in the vicinity of the peak and trough points. Moreover, in accordance with the present invention, the detector 12 performs sensing of the peaks and troughs solely in terms of the detection signal from the light intensity detector 11 because the apparatus shown in FIG. 5 is so designed that the intensities of the light beams having wavelengths $\lambda_1$ and $\lambda_2$ simultaneously reach their peaks and troughs.

In the next step, the $\phi$ computing circuit 16 performs the following sequence of calculations in accordance with equations (14) and (15) using the data stored in the sub-peak/trough data storage circuits 13 and 14. In the sequence of calculations given below, the intensities of light detected at points A to F and G to K are designated by the same symbols. A to F and G to K;

$$\Phi_{11} = \{(A - D)/D\}/\{(G - J)/J\}$$
$$\Phi_{12} = \{(A - E)/E\}/\{(G - K)/K\}$$
$$\Phi_{13} = \{(A - F)/F\}/\{(G - L)/L\}$$
$$\Phi_{21} = \{(B - D)/D\}/\{(H - J)/J\}$$
$$\vdots$$
$$\Phi_{33} = \{(C - F)/F\}/\{(I - L)/L\}$$

First, the $\phi$ computing circuit 16 determines $\phi_{11}$ from the intensities of light A, D having the wavelength $\lambda_2$ that are detected at time $T_1$ and $T_4$, and from the intensities of light G, J having the wavelength $\lambda_1$ that are detected at times $T_1$ and $T_4$. Then, the circuit 16 determines $\phi_{12}$ from the intensities of light A, E having the wavelength $\lambda_2$ that are detected at times $T_1$ and $T_5$, and from the quantities of light G, K having the wavelength $\lambda_1$ that are detected at times $T_1$ and $T_5$. After repeating these procedures, the circuit 16 finally determines $\phi_{33}$ from the quantities of light C, F having the wavelength $\lambda_2$ that are detected at times $T_3$ and $T_6$, and from the quantities of light I, L having the wavelength $\lambda_1$ that are detected at times $T_3$ and $T_6$. The thus-determined nine values of $\phi$, $\phi_{11}$, $\phi_{12}$ ... $\phi_{33}$ are then averaged by the mean $\phi$ computing circuit 17 which calculates $(\phi_{11}+\phi_{12}+ \ldots +\phi_{33})/9$.

On the basis of the thus-obtained average $\phi_A$ and data stored preliminarily (e.g., $E_1$, $E_r$ and $E_0$ shown in FIG. 3), the S computing circuit 18 computes the oxygen saturation S and outputs it to an external circuit such as a display.

The apparatus described above has the advantage that it requires only a simple circuit to determine the accurate value of the oxygen saturation.

The apparatus shown in FIG. 5 employs the first and second light quantity detectors 10 and 11 for detecting the intensities of the light beams having different wavelengths of $\lambda_1$ and $\lambda_2$. However, the present invention can be practiced using a single light intensity detector if the apparatus is designed to operate on a time sharing basis in which light beams having wavelengths $\lambda_1$ and $\lambda_2$ are received alternately rather than simultaneously.

The apparatus shown in FIG. 5 processes the output signals from the light intensity detectors in analog form. If desired, the output signals from the light intensity detectors can be processed after being converted to digital signals by an A/D converter. The apparatus may be designed in such a manner that the digital signals obtained by the A/D converter are processed with a microcomputer.

In an illustrative method for computing $\phi_{11}$, $\phi_{12}$ ... with the aid of a microcomputer, at least one cycle of the output signals from the light intensity detectors is stored, the times at which the peak and trough occur in the waveform are detected, a plurality of points in time that fall in the vicinity of each of the peak and trough are detected, $\phi_{11}$, $\phi_{12}$ ... are determined on the basis of the values of the signals detected at these points in time.

In the embodiment described above, the computation of the oxygen saturation S is preceded by the averaging of individually determined values of $\phi$. Alternatively, a plurality of values of S may be determined and then averaged.

As described in the foregoing, the apparatus of the present invention determines the average concentration of a light-absorbing material in blood on the basis of a plurality of values in the vicinity of the peak and trough of a detection signal from a light intensity detector. This is effective not only in minimizing the adverse effects of noise present in the detection signal, but also in producing highly precise measurement values under all conditions.

What is claimed is:

1. An apparatus for determining the concentration of a light-absorbing material in blood based on a differential amount of transmission of light of different wavelengths passing through a living tissue due to blood pulsations, said apparatus comprising: a light intensity detector for detecting the intensity of said light passing through said tissue; time point detecting means for detecting, for each wavelength of light, a plurality of points in time that fall in the vicinity of one peak and one trough of a detection signal produced by said light intensity detector; memory means for storing, for each wavelength of light, values of said detection signals produced at each of said points in time as detected by said time point detecting means; and concentration computing means for computing a concentration of a light-absorbing material in blood in said tissue in response to the values of said detection signals stored by said memory means.

2. The apparatus for determining the concentration of a light-absorbing material in blood as recited in claim 1, wherein said concentration computing means samples, for each wavelength of light, a plurality of combinations of detection signals from the values of detection signals stored in said memory means, said detection signals being produced from said light intensity detector at a point in time in the vicinity of the peak and at a point in time in the vicinity of the trough, said concentration computing means comprising means for computing the concentration of the light-absorbing material in blood for each combination of detection signals, and for calculating the average of the results of said computation.

3. The apparatus for determining the concentration of a light-absorbing material in blood as recited in claim 1, wherein said concentration computing means comprise means for sampling, for each wavelength of light, a plurality of combinations of detection signals from the values of detection signals stored in said memory means, said detection signals being produced from said light intensity detector at a point in time in the vicinity of said peak and at a point in time in the vicinity of said trough, and said concentration computing means comprising means for performing a predetermined sequence of calculations for the respective combinations of detection signals, averaging the results of these calculations, and computing the concentration of the light-absorbing material in blood on the basis of the resulting average.

* * * * *